US012372782B2

(12) United States Patent
Zare Seisan

(10) Patent No.: US 12,372,782 B2
(45) Date of Patent: Jul. 29, 2025

(54) AUTOMATIC MEDIA CAPTURE USING BIOMETRIC SENSOR DATA

(71) Applicant: Snap Inc., Santa Monica, CA (US)

(72) Inventor: Farid Zare Seisan, San Diego, CA (US)

(73) Assignee: Snap Inc., Santa Monica, CA (US)

( * ) Notice: Subject to any disclaimer, the term of this patent is extended or adjusted under 35 U.S.C. 154(b) by 536 days.

(21) Appl. No.: 17/716,825

(22) Filed: Apr. 8, 2022

(65) Prior Publication Data

US 2022/0373791 A1 Nov. 24, 2022

Related U.S. Application Data

(60) Provisional application No. 63/190,515, filed on May 19, 2021.

(51) Int. Cl.
*G02B 27/00* (2006.01)
*G02B 27/01* (2006.01)
*G06V 40/16* (2022.01)
*G06V 40/20* (2022.01)
*H04R 3/00* (2006.01)

(52) U.S. Cl.
CPC ....... *G02B 27/0093* (2013.01); *G02B 27/017* (2013.01); *G06V 40/164* (2022.01); *G06V 40/23* (2022.01); *H04R 3/005* (2013.01); *G02B 2027/0138* (2013.01)

(58) Field of Classification Search
None
See application file for complete search history.

(56) References Cited

U.S. PATENT DOCUMENTS

| 8,934,015 | B1* | 1/2015 | Chi | G06F 16/955 |
| | | | | 348/158 |
| 11,924,376 | B2* | 3/2024 | Anderson | H04M 3/42357 |
| 2008/0177194 | A1* | 7/2008 | Zhang | A61N 1/365 |
| | | | | 600/513 |
| 2012/0206323 | A1* | 8/2012 | Osterhout | G06Q 30/02 |
| | | | | 345/8 |
| 2014/0031001 | A1 | 1/2014 | Jacobsen | |
| 2015/0063776 | A1 | 3/2015 | Ross et al. | |
| 2015/0084857 | A1 | 3/2015 | Kimura | |

(Continued)

FOREIGN PATENT DOCUMENTS

| CN | 117321545 A | 12/2023 |
| CN | 117321548 A | 12/2023 |

(Continued)

OTHER PUBLICATIONS

"International Application Serial No. PCT/US2022/029642, International Search Report mailed Sep. 6, 2022", 4 pgs.

(Continued)

*Primary Examiner* — Samah A Beg
(74) *Attorney, Agent, or Firm* — Schwegman Lundberg & Woessner, P.A.

(57) ABSTRACT

Systems and methods herein describe a media capture system that receives sensor data from biometric sensors coupled to a head-wearable apparatus, detects a trigger event corresponding to a user of the head-wearable apparatus based on the sensor data, captures images using a camera coupled to the head-wearable apparatus, and transmits the captured images to a client device.

20 Claims, 9 Drawing Sheets

(56) References Cited

U.S. PATENT DOCUMENTS

| | | | |
|---|---|---|---|
| 2015/0324636 A1* | 11/2015 | Bentley | A63F 13/212 386/227 |
| 2017/0365101 A1* | 12/2017 | Samec | G06T 19/006 |
| 2018/0256115 A1* | 9/2018 | Campbell | A61B 5/4023 |
| 2020/0124845 A1 | 4/2020 | Smith et al. | |
| 2021/0173480 A1 | 6/2021 | Osterhout et al. | |
| 2022/0375103 A1 | 11/2022 | Zare Seisan | |

FOREIGN PATENT DOCUMENTS

| | | |
|---|---|---|
| WO | WO-2017011817 A1 | 1/2017 |
| WO | WO-2022245831 A1 | 11/2022 |
| WO | WO-2022245856 A1 | 11/2022 |

OTHER PUBLICATIONS

"International Application Serial No. PCT/US2022/029642, Written Opinion mailed Sep. 6, 2022", 6 pgs.

"U.S. Appl. No. 17/716,777, Advisory Action mailed Feb. 18, 2025", 3 pgs.

"U.S. Appl. No. 17/716,777, Examiner Interview Summary mailed Jan. 27, 2025", 2 pgs.

"U.S. Appl. No. 17/716,777, Examiner Interview Summary mailed Nov. 26, 2024", 2 pgs.

"U.S. Appl. No. 17/716,777, Final Office Action mailed Dec. 16, 2024", 14 pgs.

"U.S. Appl. No. 17/716,777, Non Final Office Action mailed Aug. 28, 2024", 18 pgs.

"U.S. Appl. No. 17/716,777, Response filed Jan. 29, 2025 to Final Office Action mailed Dec. 16, 2024", 8 pgs.

"U.S. Appl. No. 17/716,777, Response filed Nov. 26, 2024 to Non Final Office Action mailed Aug. 28, 2024", 9 pgs.

"International Application Serial No. PCT/US2022/029642, International Preliminary Report on Patentability mailed Nov. 30, 2023", 8 pgs.

"International Application Serial No. PCT/US2022/029675, International Preliminary Report on Patentability mailed Nov. 30, 2023", 8 pgs.

"International Application Serial No. PCT/US2022/029675, International Search Report mailed Sep. 1, 2022", 4 pgs.

"International Application Serial No. PCT/US2022/029675, Written Opinion mailed Sep. 1, 2022", 6 pgs.

Ishimaru, Shoya, et al., "In the Blink of an Eye—Combining Head Motion and Eye Blink Frequency for Activity Recognition with Google Glass", Proceedings of the 5th augmented human international conference, (2014), 4 pgs.

* cited by examiner

AUTOMATIC MEDIA CAPTURE USING BIOMETRIC SENSOR DATA

CLAIM OF PRIORITY

This application claims the benefit of priority to U.S. Provisional Application Ser. No. 63/190,515, filed May 19, 2021, which is incorporated herein by reference in its entirety.

TECHNICAL FIELD

Embodiments herein generally relate to augmented reality. More specifically, but not by way of limitation, embodiments herein describe automatic media capture on an augmented reality device using biometric sensor data.

BACKGROUND

Augmented reality (AR) allows users to interact with the real-world. Users can render digital content onto real-world objects and can enhance their experience with the physical world.

BRIEF DESCRIPTION OF THE SEVERAL VIEWS OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some non-limiting examples are illustrated in the figures of the accompanying drawings in which.

DETAILED DESCRIPTION

Embodiments of the present disclosure describe a media capture system for automatically and intelligently capturing images based on detecting a sudden change in biometric sensor data received at a wearable device. For example, the media capture system automatically records and transmits a threatening or emergency event to one or more computing devices based on a sudden change of a user's health condition.

Networked Computing Environment

Figure 1:
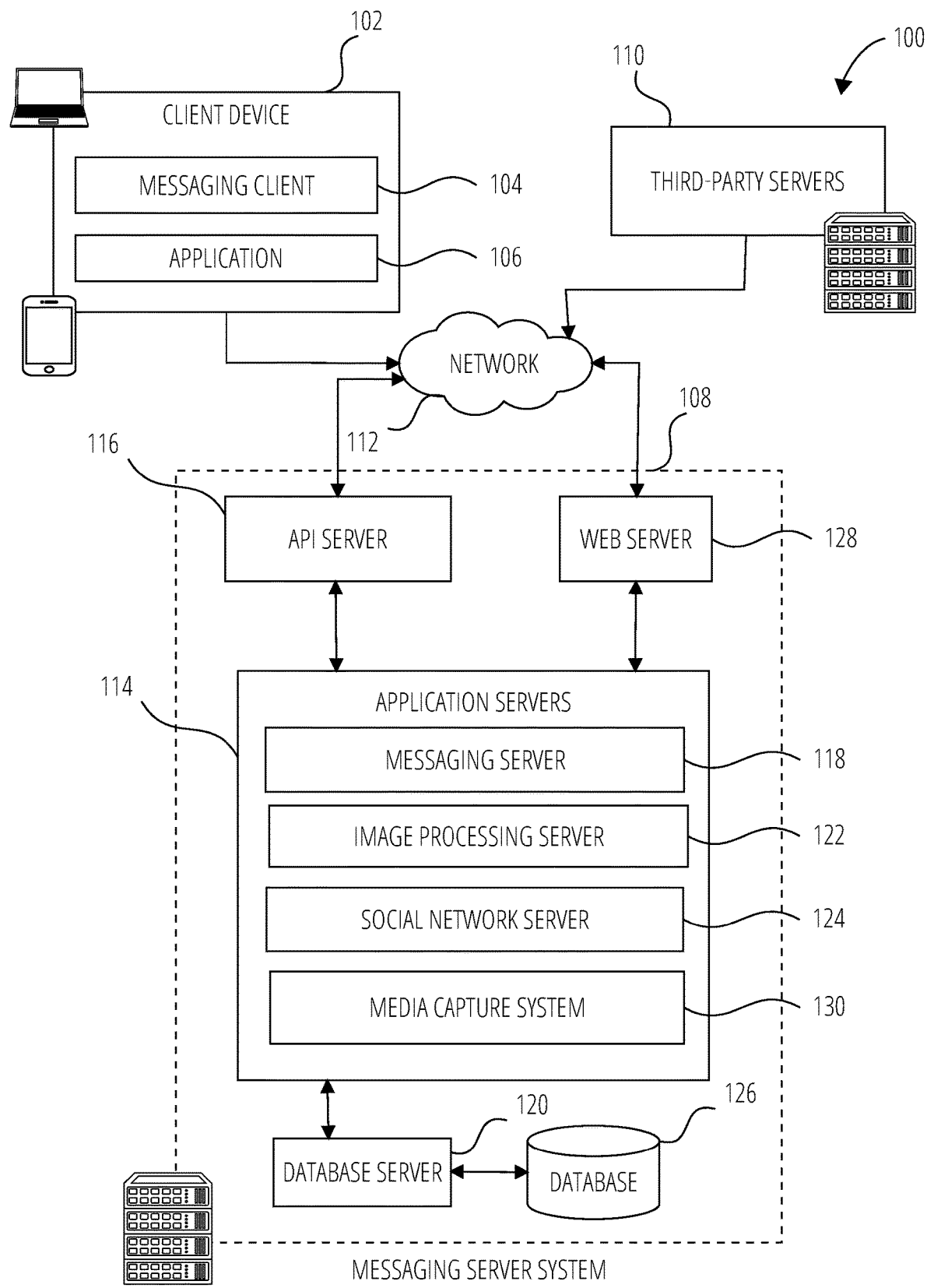
FIG. 1 is a diagrammatic representation of a networked environment in which the present disclosure may be deployed, in accordance with some examples.

FIG. 1 is a block diagram showing an example messaging system 100 for exchanging data (e.g., messages and associated content) over a network. The messaging system 100 includes multiple instances of a client device 102, each of which hosts a number of applications, including a messaging client 104 and other applications 106. Each messaging client 104 is communicatively coupled to other instances of the messaging client 104 (e.g., hosted on respective other client devices 102), a messaging server system 108 and third-party servers 110 via a network 112 (e.g., the Internet). A messaging client 104 can also communicate with locally-hosted applications 106 using Applications Program Interfaces (APIs).

A messaging client 104 is able to communicate and exchange data with other messaging clients 104 and with the messaging server system 108 via the network 112. The data exchanged between messaging clients 104, and between a messaging client 104 and the messaging server system 108, includes functions (e.g., commands to invoke functions) as well as payload data (e.g., text, audio, video or other multimedia data).

The messaging server system 108 provides server-side functionality via the network 112 to a particular messaging client 104. While certain functions of the messaging system 100 are described herein as being performed by either a messaging client 104 or by the messaging server system 108, the location of certain functionality either within the messaging client 104 or the messaging server system 108 may be a design choice. For example, it may be technically preferable to initially deploy certain technology and functionality within the messaging server system 108 but to later migrate this technology and functionality to the messaging client 104 where a client device 102 has sufficient processing capacity.

The messaging server system 108 supports various services and operations that are provided to the messaging client 104. Such operations include transmitting data to, receiving data from, and processing data generated by the messaging client 104. This data may include message content, client device information, geolocation information, media augmentation and overlays, message content persistence conditions, social network information, and live event information, as examples. Data exchanges within the messaging system 100 are invoked and controlled through functions available via user interfaces (UIs) of the messaging client 104.

Turning now specifically to the messaging server system 108, an Application Program Interface (API) server 116 is coupled to, and provides a programmatic interface to, application servers 114. The application servers 114 are communicatively coupled to a database server 120, which facilitates access to a database 126 that stores data associated with messages processed by the application servers 114. Similarly, a web server 128 is coupled to the application servers 114, and provides web-based interfaces to the application servers 114. To this end, the web server 128 processes incoming network requests over the Hypertext Transfer Protocol (HTTP) and several other related protocols.

The Application Program Interface (API) server 116 receives and transmits message data (e.g., commands and message payloads) between the client device 102 and the application servers 114. Specifically, the Application Program Interface (API) server 116 provides a set of interfaces (e.g., routines and protocols) that can be called or queried by the messaging client 104 in order to invoke functionality of the application servers 114. The Application Program Interface (API) server 116 exposes various functions supported by the application servers 114, including account registration, login functionality, the sending of messages, via the application servers 114, from a particular messaging client 104 to another messaging client 104, the sending of media files (e.g., images or video) from a messaging client 104 to a messaging server 118, and for possible access by another messaging client 104, the settings of a collection of media data (e.g., story), the retrieval of a list of friends of a user of a client device 102, the retrieval of such collections, the retrieval of messages and content, the addition and deletion of entities (e.g., friends) to an entity graph (e.g., a social graph), the location of friends within a social graph, and opening an application event (e.g., relating to the messaging client 104).

The application servers 114 host a number of server applications and subsystems, including for example a messaging server 118, an image processing server 122, a social network server 124 and a Media capture system 130. The messaging server 118 implements a number of message processing technologies and functions, particularly related to the aggregation and other processing of content (e.g., textual and multimedia content) included in messages received from multiple instances of the messaging client 104. As will be described in further detail, the text and media content from multiple sources may be aggregated into collections of content (e.g., called stories or galleries). These collections are then made available to the messaging client 104. Other processor and memory intensive processing of data may also be performed server-side by the messaging server 118, in view of the hardware requirements for such processing.

The application servers 114 also include an image processing server 122 that is dedicated to performing various image processing operations, typically with respect to images or video within the payload of a message sent from or received at the messaging server 118.

Figure 3:
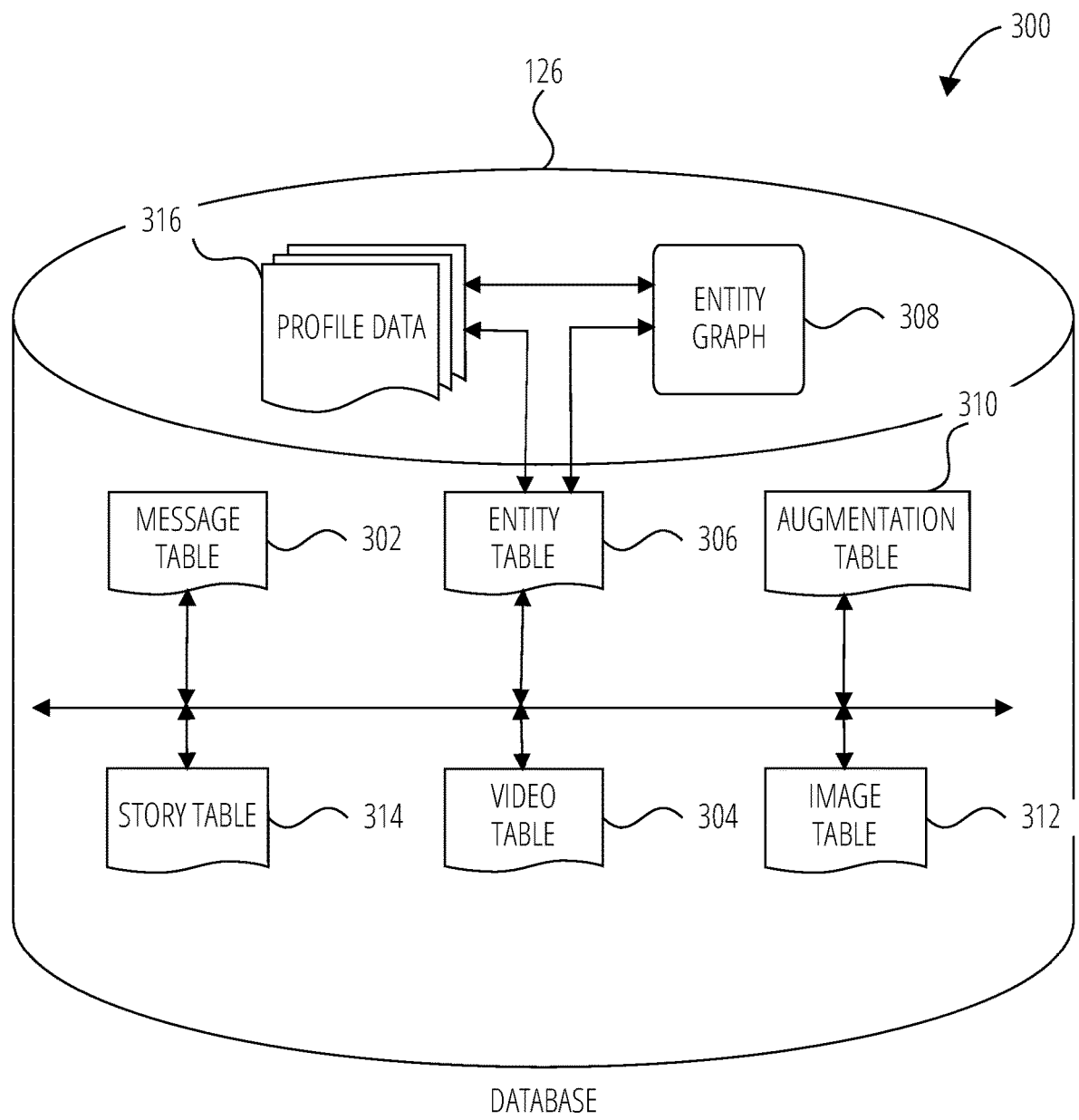
FIG. 3 is a diagrammatic representation of a data structure as maintained in a database, in accordance with some examples.

The social network server 124 supports various social networking functions and services and makes these functions and services available to the messaging server 118. To this end, the social network server 124 maintains and accesses an entity graph 308 (as shown in FIG. 3) within the database 126. Examples of functions and services supported by the social network server 124 include the identification of other users of the messaging system 100 with which a particular user has relationships or is "following," and also the identification of other entities and interests of a particular user.

The Media capture system 130 automatically and intelligently captures image or video based on detecting a change in biometric sensor data of a user of a wearable device. For example, the wearable device automatically records a threatening or emergency event based on a sudden change in biometric sensor data.

Returning to the messaging client 104, features and functions of an external resource (e.g., an application 106 or applet) are made available to a user via an interface of the messaging client 104. In this context, "external" refers to the fact that the application 106 or applet is external to the messaging client 104. The external resource is often provided by a third party but may also be provided by the creator or provider of the messaging client 104. The messaging client 104 receives a user selection of an option to launch or access features of such an external resource. The external resource may be the application 106 installed on the client device 102 (e.g., a "native app"), or a small-scale version of the application (e.g., an "applet") that is hosted on the client device 102 or remote of the client device 102 (e.g., on third-party servers 110). The small-scale version of the application includes a subset of features and functions of the application (e.g., the full-scale, native version of the application) and is implemented using a markup-language document. In one example, the small-scale version of the application (e.g., an "applet") is a web-based, markup-language version of the application and is embedded in the messaging client 104. In addition to using markup-language documents (e.g., a .*ml file), an applet may incorporate a scripting language (e.g., a .*js file or a .json file) and a style sheet (e.g., a .*ss file).

In response to receiving a user selection of the option to launch or access features of the external resource, the messaging client 104 determines whether the selected external resource is a web-based external resource or a locally-installed application 106. In some cases, applications 106 that are locally installed on the client device 102 can be launched independently of and separately from the messaging client 104, such as by selecting an icon, corresponding to the application 106, on a home screen of the client device 102. Small-scale versions of such applications can be launched or accessed via the messaging client 104 and, in some examples, no or limited portions of the small-scale application can be accessed outside of the messaging client 104. The small-scale application can be launched by the messaging client 104 receiving, from a third-party server 110 for example, a markup-language document associated with the small-scale application and processing such a document.

In response to determining that the external resource is a locally-installed application 106, the messaging client 104 instructs the client device 102 to launch the external resource by executing locally-stored code corresponding to the external resource. In response to determining that the external resource is a web-based resource, the messaging client 104 communicates with the third-party servers 110 (for example) to obtain a markup-language document corresponding to the selected external resource. The messaging client 104 then processes the obtained markup-language document to present the web-based external resource within a user interface of the messaging client 104.

The messaging client 104 can notify a user of the client device 102, or other users related to such a user (e.g., "friends"), of activity taking place in one or more external resources. For example, the messaging client 104 can provide participants in a conversation (e.g., a chat session) in the messaging client 104 with notifications relating to the current or recent use of an external resource by one or more members of a group of users. One or more users can be invited to join in an active external resource or to launch a recently-used but currently inactive (in the group of friends) external resource. The external resource can provide participants in a conversation, each using respective messaging clients 104, with the ability to share an item, status, state, or location in an external resource with one or more members of a group of users into a chat session. The shared item may be an interactive chat card with which members of the chat can interact, for example, to launch the corresponding external resource, view specific information within the external resource, or take the member of the chat to a specific location or state within the external resource. Within a given external resource, response messages can be sent to users on the messaging client 104. The external resource can selectively include different media items in the responses, based on a current context of the external resource.

The messaging client 104 can present a list of the available external resources (e.g., applications 106 or applets) to a user to launch or access a given external resource. This list can be presented in a context-sensitive menu. For example, the icons representing different ones of the application 106 (or applets) can vary based on how the menu is launched by the user (e.g., from a conversation interface or from a non-conversation interface).

System Architecture

Figure 2:
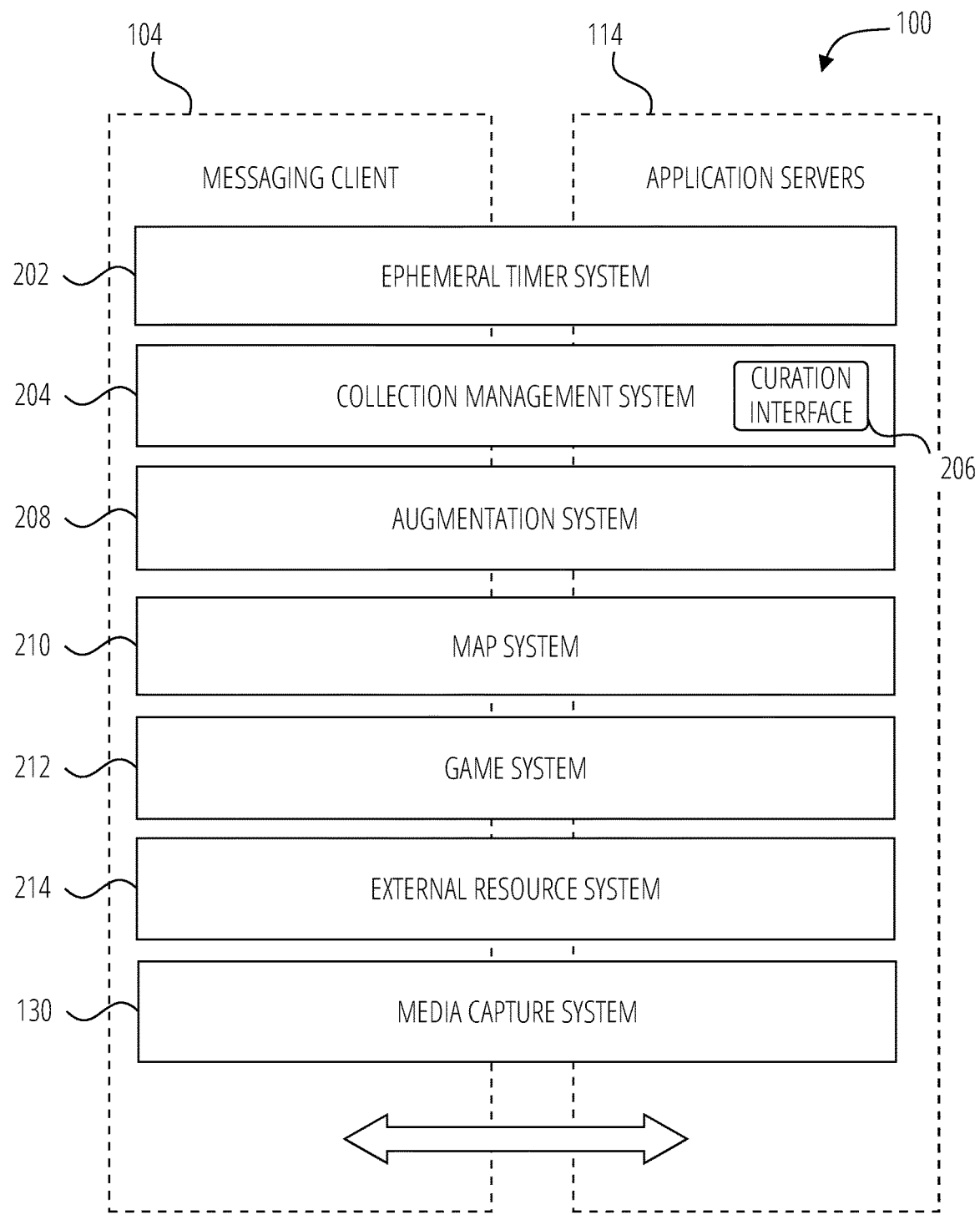
FIG. 2 is a diagrammatic representation of a messaging system, in accordance with some examples, that has both client-side and server-side functionality.

FIG. 2 is a block diagram illustrating further details regarding the messaging system 100, according to some examples. Specifically, the messaging system 100 is shown to comprise the messaging client 104 and the application servers 114. The messaging system 100 embodies a number of subsystems, which are supported on the client-side by the messaging client 104 and on the sever-side by the application servers 114. These subsystems include, for example, an ephemeral timer system 202, a collection management system 204, an augmentation system 208, a map system 210, a game system 212, and an external resource system 214.

The ephemeral timer system 202 is responsible for enforcing the temporary or time-limited access to content by the messaging client 104 and the messaging server 118. The ephemeral timer system 202 incorporates a number of timers that, based on duration and display parameters associated with a message, or collection of messages (e.g., a story), selectively enable access (e.g., for presentation and display) to messages and associated content via the messaging client 104. Further details regarding the operation of the ephemeral timer system 202 are provided below.

The collection management system 204 is responsible for managing sets or collections of media (e.g., collections of text, image video, and audio data). A collection of content (e.g., messages, including images, video, text, and audio) may be organized into an "event gallery" or an "event story." Such a collection may be made available for a specified time period, such as the duration of an event to which the content relates. For example, content relating to a music concert may be made available as a "story" for the duration of that music concert. The collection management system 204 may also be responsible for publishing an icon that provides notification of the existence of a particular collection to the user interface of the messaging client 104.

The collection management system 204 furthermore includes a curation interface 206 that allows a collection manager to manage and curate a particular collection of content. For example, the curation interface 206 enables an event organizer to curate a collection of content relating to a specific event (e.g., delete inappropriate content or redundant messages). Additionally, the collection management system 204 employs machine vision (or image recognition technology) and content rules to automatically curate a content collection. In certain examples, compensation may be paid to a user for the inclusion of user-generated content into a collection. In such cases, the collection management system 204 operates to automatically make payments to such users for the use of their content.

The augmentation system 208 provides various functions that enable a user to augment (e.g., annotate or otherwise modify or edit) media content associated with a message. For example, the augmentation system 208 provides functions related to the generation and publishing of media overlays for messages processed by the messaging system 100. The augmentation system 208 operatively supplies a media overlay or augmentation (e.g., an image filter) to the messaging client 104 based on a geolocation of the client device 102. In another example, the augmentation system 208 operatively supplies a media overlay to the messaging client 104 based on other information, such as social network information of the user of the client device 102. A media overlay may include audio and visual content and visual effects. Examples of audio and visual content include pictures, texts, logos, animations, and sound effects. An example of a visual effect includes color overlaying. The audio and visual content or the visual effects can be applied to a media content item (e.g., a photo) at the client device 102. For example, the media overlay may include text or image that can be overlaid on top of a photograph taken by the client device 102. In another example, the media overlay includes an identification of a location overlay (e.g., Venice beach), a name of a live event, or a name of a merchant overlay (e.g., Beach Coffee House). In another example, the augmentation system 208 uses the geolocation of the client device 102 to identify a media overlay that includes the name of a merchant at the geolocation of the client device 102. The media overlay may include other indicia associated with the merchant. The media overlays may be stored in the database 126 and accessed through the database server 120.

In some examples, the augmentation system 208 provides a user-based publication platform that enables users to select a geolocation on a map and upload content associated with the selected geolocation. The user may also specify circumstances under which a particular media overlay should be offered to other users. The augmentation system 208 generates a media overlay that includes the uploaded content and associates the uploaded content with the selected geolocation.

In other examples, the augmentation system 208 provides a merchant-based publication platform that enables merchants to select a particular media overlay associated with a geolocation via a bidding process. For example, the augmentation system 208 associates the media overlay of the highest bidding merchant with a corresponding geolocation for a predefined amount of time.

The map system 210 provides various geographic location functions, and supports the presentation of map-based media content and messages by the messaging client 104. For example, the map system 210 enables the display of user icons or avatars (e.g., stored in profile data 316) on a map to indicate a current or past location of "friends" of a user, as well as media content (e.g., collections of messages including photographs and videos) generated by such friends, within the context of a map. For example, a message posted by a user to the messaging system 100 from a specific geographic location may be displayed within the context of a map at that particular location to "friends" of a specific user on a map interface of the messaging client 104. A user can furthermore share his or her location and status information (e.g., using an appropriate status avatar) with other users of the messaging system 100 via the messaging client 104, with this location and status information being similarly displayed within the context of a map interface of the messaging client 104 to selected users.

The game system 212 provides various gaming functions within the context of the messaging client 104. The messaging client 104 provides a game interface providing a list of available games that can be launched by a user within the context of the messaging client 104, and played with other users of the messaging system 100. The messaging system 100 further enables a particular user to invite other users to participate in the play of a specific game, by issuing invitations to such other users from the messaging client 104. The messaging client 104 also supports both the voice and text messaging (e.g., chats) within the context of gameplay, provides a leaderboard for the games, and also supports the provision of in-game rewards (e.g., coins and items).

The external resource system 214 provides an interface for the messaging client 104 to communicate with remote servers (e.g. third-party servers 110) to launch or access external resources, i.e. applications or applets. Each third-party server 110 hosts, for example, a markup language (e.g., HTML5) based application or small-scale version of an application (e.g., game, utility, payment, or ride-sharing application). The messaging client 104 may launches a web-based resource (e.g., application) by accessing the HTML5 file from the third-party servers 110 associated with the web-based resource. In certain examples, applications hosted by third-party servers 110 are programmed in JavaScript leveraging a Software Development Kit (SDK) provided by the messaging server 118. The SDK includes Application Programming Interfaces (APIs) with functions that can be called or invoked by the web-based application. In certain examples, the messaging server 118 includes a JavaScript library that provides a given external resource access to certain user data of the messaging client 104. HTML5 is used as an example technology for programming games, but applications and resources programmed based on other technologies can be used.

In order to integrate the functions of the SDK into the web-based resource, the SDK is downloaded by a third-party server 110 from the messaging server 118 or is otherwise received by the third-party server 110. Once downloaded or received, the SDK is included as part of the application code of a web-based external resource. The code of the web-based resource can then call or invoke certain functions of the SDK to integrate features of the messaging client 104 into the web-based resource.

The SDK stored on the messaging server 118 effectively provides the bridge between an external resource (e.g., applications 106 or applets and the messaging client 104. This provides the user with a seamless experience of communicating with other users on the messaging client 104, while also preserving the look and feel of the messaging client 104. To bridge communications between an external resource and a messaging client 104, in certain examples, the SDK facilitates communication between third-party servers 110 and the messaging client 104. In certain examples, a WebViewJavaScriptBridge running on a client device 102 establishes two one-way communication channels between an external resource and the messaging client 104. Messages are sent between the external resource and the messaging client 104 via these communication channels asynchronously. Each SDK function invocation is sent as a message and callback. Each SDK function is implemented by constructing a unique callback identifier and sending a message with that callback identifier.

By using the SDK, not all information from the messaging client 104 is shared with third-party servers 110. The SDK limits which information is shared based on the needs of the external resource. In certain examples, each third-party server 110 provides an HTML5 file corresponding to the web-based external resource to the messaging server 118. The messaging server 118 can add a visual representation (such as a box art or other graphic) of the web-based external resource in the messaging client 104. Once the user selects the visual representation or instructs the messaging client 104 through a GUI of the messaging client 104 to access features of the web-based external resource, the messaging client 104 obtains the HTML5 file and instantiates the resources necessary to access the features of the web-based external resource.

The messaging client 104 presents a graphical user interface (e.g., a landing page or title screen) for an external resource. During, before, or after presenting the landing page or title screen, the messaging client 104 determines whether the launched external resource has been previously authorized to access user data of the messaging client 104. In response to determining that the launched external resource has been previously authorized to access user data of the messaging client 104, the messaging client 104 presents another graphical user interface of the external resource that includes functions and features of the external resource. In response to determining that the launched external resource has not been previously authorized to access user data of the messaging client 104, after a threshold period of time (e.g., 3 seconds) of displaying the landing page or title screen of the external resource, the messaging client 104 slides up (e.g., animates a menu as surfacing from a bottom of the screen to a middle of or other portion of the screen) a menu for authorizing the external resource to access the user data. The menu identifies the type of user data that the external resource will be authorized to use. In response to receiving a user selection of an accept option, the messaging client 104 adds the external resource to a list of authorized external resources and allows the external resource to access user data from the messaging client 104. In some examples, the external resource is authorized by the messaging client 104 to access the user data in accordance with an OAuth 2 framework.

The messaging client 104 controls the type of user data that is shared with external resources based on the type of external resource being authorized. For example, external resources that include full-scale applications (e.g., an application 106) are provided with access to a first type of user data (e.g., only two-dimensional avatars of users with or without different avatar characteristics). As another example, external resources that include small-scale versions of applications (e.g., web-based versions of applications) are provided with access to a second type of user data (e.g., payment information, two-dimensional avatars of users, three-dimensional avatars of users, and avatars with various avatar characteristics). Avatar characteristics include different ways to customize a look and feel of an avatar, such as different poses, facial features, clothing, and so forth.

Data Architecture

FIG. 3 is a schematic diagram illustrating data structures 300, which may be stored in the database 126 of the messaging server system 108, according to certain examples. While the content of the database 126 is shown to comprise a number of tables, it will be appreciated that the data could be stored in other types of data structures (e.g., as an object-oriented database).

The database 126 includes message data stored within a message table 302. This message data includes, for any particular one message, at least message sender data, message recipient (or receiver) data, and a payload. Further details regarding information that may be included in a message, and included within the message data stored in the message table 302 is described below with reference to FIG. 4.

An entity table 306 stores entity data, and is linked (e.g., referentially) to an entity graph 308 and profile data 316. Entities for which records are maintained within the entity table 306 may include individuals, corporate entities, organizations, objects, places, events, and so forth. Regardless of entity type, any entity regarding which the messaging server system 108 stores data may be a recognized entity. Each entity is provided with a unique identifier, as well as an entity type identifier (not shown).

The entity graph 308 stores information regarding relationships and associations between entities. Such relationships may be social, professional (e.g., work at a common corporation or organization) interested-based or activity-based, merely for example.

The profile data 316 stores multiple types of profile data about a particular entity. The profile data 316 may be selectively used and presented to other users of the messaging system 100, based on privacy settings specified by a particular entity. Where the entity is an individual, the profile data 316 includes, for example, a user name, telephone number, address, settings (e.g., notification and privacy settings), as well as a user-selected avatar representation (or collection of such avatar representations). A particular user may then selectively include one or more of these avatar representations within the content of messages communicated via the messaging system 100, and on map interfaces displayed by messaging clients 104 to other users. The collection of avatar representations may include "status avatars," which present a graphical representation of a status or activity that the user may select to communicate at a particular time.

Where the entity is a group, the profile data 316 for the group may similarly include one or more avatar representations associated with the group, in addition to the group name, members, and various settings (e.g., notifications) for the relevant group.

The database 126 also stores augmentation data, such as overlays or filters, in an augmentation table 310. The augmentation data is associated with and applied to videos (for which data is stored in a video table 304) and images (for which data is stored in an image table 312).

Filters, in one example, are overlays that are displayed as overlaid on an image or video during presentation to a recipient user. Filters may be of various types, including user-selected filters from a set of filters presented to a sending user by the messaging client 104 when the sending user is composing a message. Other types of filters include geolocation filters (also known as geo-filters), which may be presented to a sending user based on geographic location. For example, geolocation filters specific to a neighborhood or special location may be presented within a user interface by the messaging client 104, based on geolocation information determined by a Global Positioning System (GPS) unit of the client device 102.

Another type of filter is a data filter, which may be selectively presented to a sending user by the messaging client 104, based on other inputs or information gathered by the client device 102 during the message creation process. Examples of data filters include current temperature at a specific location, a current speed at which a sending user is traveling, battery life for a client device 102, or the current time.

Other augmentation data that may be stored within the image table 312 includes augmented reality content items (e.g., corresponding to applying Lenses or augmented reality experiences). An augmented reality content item may be a real-time special effect and sound that may be added to an image or a video.

As described above, augmentation data includes augmented reality content items, overlays, image transformations, AR images, and similar terms refer to modifications that may be applied to image data (e.g., videos or images). This includes real-time modifications, which modify an image as it is captured using device sensors (e.g., one or multiple cameras) of a client device 102 and then displayed on a screen of the client device 102 with the modifications. This also includes modifications to stored content, such as video clips in a gallery that may be modified. For example, in a client device 102 with access to multiple augmented reality content items, a user can use a single video clip with multiple augmented reality content items to see how the different augmented reality content items will modify the stored clip. For example, multiple augmented reality content items that apply different pseudorandom movement models can be applied to the same content by selecting different augmented reality content items for the content. Similarly, real-time video capture may be used with an illustrated modification to show how video images currently being captured by sensors of a client device 102 would modify the captured data. Such data may simply be displayed on the screen and not stored in memory, or the content captured by the device sensors may be recorded and stored in memory with or without the modifications (or both). In some systems, a preview feature can show how different augmented reality content items will look within different windows in a display at the same time. This can, for example, enable multiple windows with different pseudorandom animations to be viewed on a display at the same time.

Data and various systems using augmented reality content items or other such transform systems to modify content using this data can thus involve detection of objects (e.g., faces, hands, bodies, cats, dogs, surfaces, objects, etc.), tracking of such objects as they leave, enter, and move around the field of view in video frames, and the modification or transformation of such objects as they are tracked. In various examples, different methods for achieving such transformations may be used. Some examples may involve generating a three-dimensional mesh model of the object or objects, and using transformations and animated textures of the model within the video to achieve the transformation. In other examples, tracking of points on an object may be used to place an image or texture (which may be two dimensional or three dimensional) at the tracked position. In still further examples, neural network analysis of video frames may be used to place images, models, or textures in content (e.g., images or frames of video). Augmented reality content items thus refer both to the images, models, and textures used to create transformations in content, as well as to additional modeling and analysis information needed to achieve such transformations with object detection, tracking, and placement.

Real-time video processing can be performed with any kind of video data (e.g., video streams, video files, etc.) saved in a memory of a computerized system of any kind. For example, a user can load video files and save them in a memory of a device, or can generate a video stream using sensors of the device. Additionally, any objects can be processed using a computer animation model, such as a human's face and parts of a human body, animals, or non-living things such as chairs, cars, or other objects.

In some examples, when a particular modification is selected along with content to be transformed, elements to be transformed are identified by the computing device, and then detected and tracked if they are present in the frames of the video. The elements of the object are modified according to the request for modification, thus transforming the frames of the video stream. Transformation of frames of a video stream can be performed by different methods for different kinds of transformation. For example, for transformations of frames mostly referring to changing forms of object's elements characteristic points for each element of an object are calculated (e.g., using an Active Shape Model (ASM) or other known methods). Then, a mesh based on the characteristic points is generated for each of the at least one element of the object. This mesh used in the following stage of tracking the elements of the object in the video stream. In the process of tracking, the mentioned mesh for each element is aligned with a position of each element. Then, additional points are generated on the mesh. A first set of first points is generated for each element based on a request for modification, and a set of second points is generated for each element based on the set of first points and the request for modification. Then, the frames of the video stream can be transformed by modifying the elements of the object on the basis of the sets of first and second points and the mesh. In such method, a background of the modified object can be changed or distorted as well by tracking and modifying the background.

In some examples, transformations changing some areas of an object using its elements can be performed by calculating characteristic points for each element of an object and generating a mesh based on the calculated characteristic points. Points are generated on the mesh, and then various areas based on the points are generated. The elements of the object are then tracked by aligning the area for each element with a position for each of the at least one element, and properties of the areas can be modified based on the request for modification, thus transforming the frames of the video stream. Depending on the specific request for modification properties of the mentioned areas can be transformed in different ways. Such modifications may involve changing color of areas; removing at least some part of areas from the frames of the video stream; including one or more new objects into areas which are based on a request for modification; and modifying or distorting the elements of an area or object. In various examples, any combination of such modifications or other similar modifications may be used. For certain models to be animated, some characteristic points can be selected as control points to be used in determining the entire state-space of options for the model animation.

In some examples of a computer animation model to transform image data using face detection, the face is detected on an image with use of a specific face detection algorithm (e.g., Viola-Jones). Then, an Active Shape Model (ASM) algorithm is applied to the face region of an image to detect facial feature reference points.

Other methods and algorithms suitable for face detection can be used. For example, in some examples, features are located using a landmark, which represents a distinguishable point present in most of the images under consideration. For facial landmarks, for example, the location of the left eye pupil may be used. If an initial landmark is not identifiable (e.g., if a person has an eyepatch), secondary landmarks may be used. Such landmark identification procedures may be used for any such objects. In some examples, a set of landmarks forms a shape. Shapes can be represented as vectors using the coordinates of the points in the shape. One shape is aligned to another with a similarity transform (allowing translation, scaling, and rotation) that minimizes the average Euclidean distance between shape points. The mean shape is the mean of the aligned training shapes.

In some examples, a search for landmarks from the mean shape aligned to the position and size of the face determined by a global face detector is started. Such a search then repeats the steps of suggesting a tentative shape by adjusting the locations of shape points by template matching of the image texture around each point and then conforming the tentative shape to a global shape model until convergence occurs. In some systems, individual template matches are unreliable, and the shape model pools the results of the weak template matches to form a stronger overall classifier. The entire search is repeated at each level in an image pyramid, from coarse to fine resolution.

A transformation system can capture an image or video stream on a client device (e.g., the client device 102) and perform complex image manipulations locally on the client device 102 while maintaining a suitable user experience, computation time, and power consumption. The complex image manipulations may include size and shape changes, emotion transfers (e.g., changing a face from a frown to a smile), state transfers (e.g., aging a subject, reducing apparent age, changing gender), style transfers, graphical element application, and any other suitable image or video manipulation implemented by a convolutional neural network that has been configured to execute efficiently on the client device 102.

In some examples, a computer animation model to transform image data can be used by a system where a user may capture an image or video stream of the user (e.g., a selfie) using a client device 102 having a neural network operating as part of a messaging client 104 operating on the client device 102. The transformation system operating within the messaging client 104 determines the presence of a face within the image or video stream and provides modification icons associated with a computer animation model to transform image data, or the computer animation model can be present as associated with an interface described herein. The modification icons include changes that may be the basis for modifying the user's face within the image or video stream as part of the modification operation. Once a modification icon is selected, the transform system initiates a process to convert the image of the user to reflect the selected modification icon (e.g., generate a smiling face on the user). A modified image or video stream may be presented in a graphical user interface displayed on the client device 102 as soon as the image or video stream is captured, and a specified modification is selected. The transformation system may implement a complex convolutional neural network on a portion of the image or video stream to generate and apply the selected modification. That is, the user may capture the image or video stream and be presented with a modified result in real-time or near real-time once a modification icon has been selected. Further, the modification may be persistent while the video stream is being captured, and the selected modification icon remains toggled. Machine taught neural networks may be used to enable such modifications.

The graphical user interface, presenting the modification performed by the transform system, may supply the user with additional interaction options. Such options may be based on the interface used to initiate the content capture and selection of a particular computer animation model (e.g., initiation from a content creator user interface). In various examples, a modification may be persistent after an initial selection of a modification icon. The user may toggle the modification on or off by tapping or otherwise selecting the face being modified by the transformation system and store it for later viewing or browse to other areas of the imaging application. Where multiple faces are modified by the transformation system, the user may toggle the modification on or off globally by tapping or selecting a single face modified and displayed within a graphical user interface. In some examples, individual faces, among a group of multiple faces, may be individually modified, or such modifications may be individually toggled by tapping or selecting the individual face or a series of individual faces displayed within the graphical user interface.

A story table 314 stores data regarding collections of messages and associated image, video, or audio data, which are compiled into a collection (e.g., a story or a gallery). The creation of a particular collection may be initiated by a particular user (e.g., each user for which a record is maintained in the entity table 306). A user may create a "personal story" in the form of a collection of content that has been created and sent/broadcast by that user. To this end, the user interface of the messaging client 104 may include an icon that is user-selectable to enable a sending user to add specific content to his or her personal story.

A collection may also constitute a "live story," which is a collection of content from multiple users that is created manually, automatically, or using a combination of manual and automatic techniques. For example, a "live story" may constitute a curated stream of user-submitted content from varies locations and events. Users whose client devices have location services enabled and are at a common location event at a particular time may, for example, be presented with an option, via a user interface of the messaging client 104, to contribute content to a particular live story. The live story may be identified to the user by the messaging client 104, based on his or her location. The end result is a "live story" told from a community perspective.

A further type of content collection is known as a "location story," which enables a user whose client device 102 is located within a specific geographic location (e.g., on a college or university campus) to contribute to a particular collection. In some examples, a contribution to a location story may require a second degree of authentication to verify that the end user belongs to a specific organization or other entity (e.g., is a student on the university campus).

As mentioned above, the video table 304 stores video data that, in one example, is associated with messages for which records are maintained within the message table 302. Similarly, the image table 312 stores image data associated with messages for which message data is stored in the entity table 306. The entity table 306 may associate various augmentations from the augmentation table 310 with various images and videos stored in the image table 312 and the video table 304.

Data Communications Architecture

Figure 4:
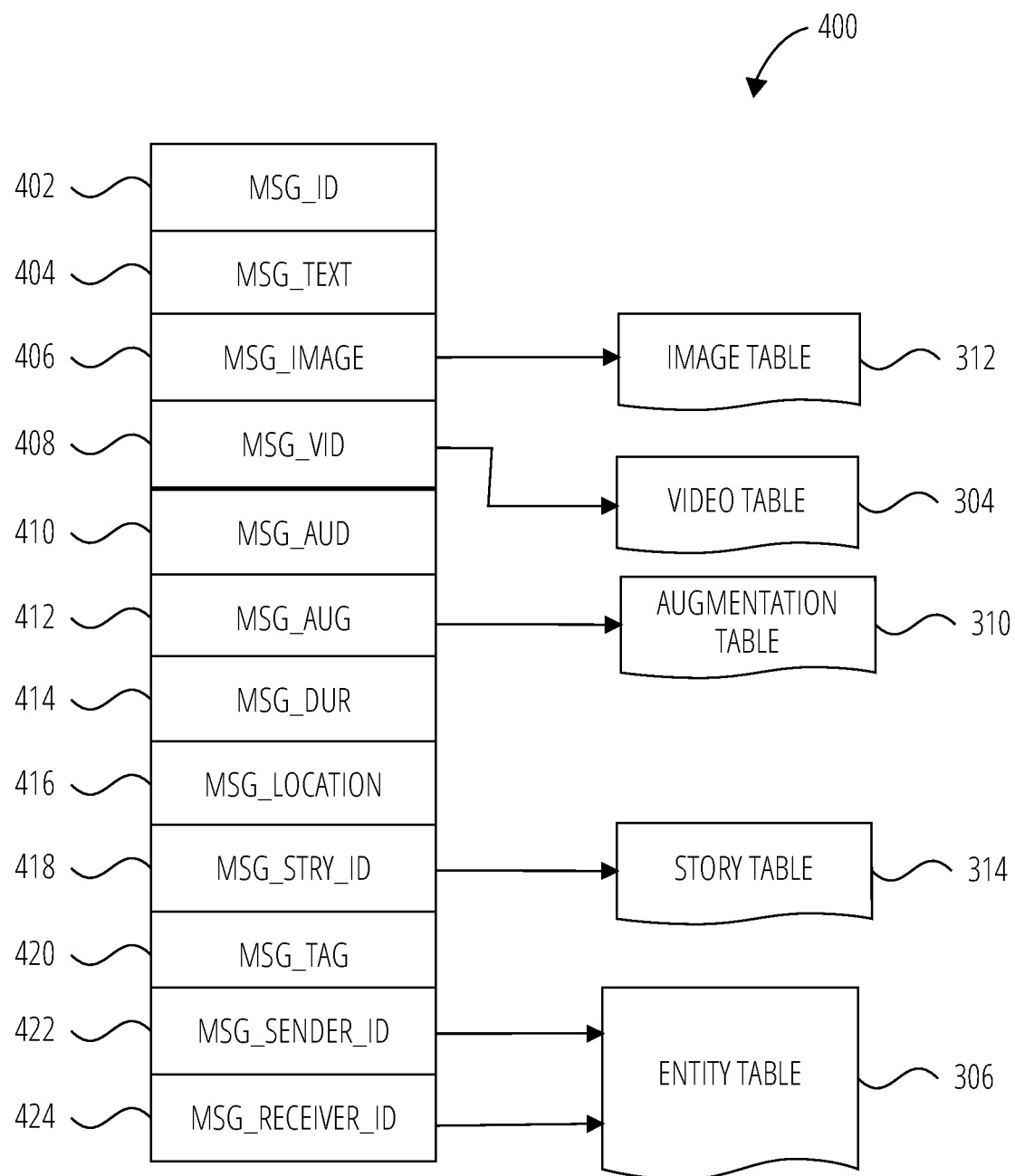
FIG. 4 is a diagrammatic representation of a message, in accordance with some examples.

FIG. 4 is a schematic diagram illustrating a structure of a message 400, according to some examples, generated by a messaging client 104 for communication to a further messaging client 104 or the messaging server 118. The content of a particular message 400 is used to populate the message table 302 stored within the database 126, accessible by the messaging server 118. Similarly, the content of a message 400 is stored in memory as "in-transit" or "in-flight" data of the client device 102 or the application servers 114. A message 400 is shown to include the following example components:

- message identifier 402: a unique identifier that identifies the message 400.
- message text payload 404: text, to be generated by a user via a user interface of the client device 102, and that is included in the message 400.
- message image payload 406: image data, captured by a camera component of a client device 102 or retrieved from a memory component of a client device 102, and that is included in the message 400. Image data for a sent or received message 400 may be stored in the image table 312.
- message video payload 408: video data, captured by a camera component or retrieved from a memory component of the client device 102, and that is included in the message 400. Video data for a sent or received message 400 may be stored in the video table 304.
- message audio payload 410: audio data, captured by a microphone or retrieved from a memory component of the client device 102, and that is included in the message 400.
- message augmentation data 412: augmentation data (e.g., filters, stickers, or other annotations or enhancements) that represents augmentations to be applied to message image payload 406, message video payload 408, or message audio payload 410 of the message 400. Augmentation data for a sent or received message 400 may be stored in the augmentation table 310.
- message duration parameter 414: parameter value indicating, in seconds, the amount of time for which content of the message (e.g., the message image payload 406, message video payload 408, message audio payload 410) is to be presented or made accessible to a user via the messaging client 104.
- message geolocation parameter 416: geolocation data (e.g., latitudinal and longitudinal coordinates) associated with the content payload of the message. Multiple message geolocation parameter 416 values may be included in the payload, each of these parameter values being associated with respect to content items included in the content (e.g., a specific image into within the message image payload 406, or a specific video in the message video payload 408).
- message story identifier 418: identifier values identifying one or more content collections (e.g., "stories" identified in the story table 314) with which a particular content item in the message image payload 406 of the message 400 is associated. For example, multiple images within the message image payload 406 may each be associated with multiple content collections using identifier values.
- message tag 420: each message 400 may be tagged with multiple tags, each of which is indicative of the subject matter of content included in the message payload. For example, where a particular image included in the message image payload 406 depicts an animal (e.g., a lion), a tag value may be included within the message tag 420 that is indicative of the relevant animal. Tag values may be generated manually, based on user input, or may be automatically generated using, for example, image recognition.
- message sender identifier 422: an identifier (e.g., a messaging system identifier, email address, or device identifier) indicative of a user of the Client device 102 on which the message 400 was generated and from which the message 400 was sent.
- message receiver identifier 424: an identifier (e.g., a messaging system identifier, email address, or device identifier) indicative of a user of the client device 102 to which the message 400 is addressed.

The contents (e.g., values) of the various components of message 400 may be pointers to locations in tables within which content data values are stored. For example, an image value in the message image payload 406 may be a pointer to (or address of) a location within an image table 312.

Similarly, values within the message video payload 408 may point to data stored within a video table 304, values stored within the message augmentations 412 may point to data stored in an augmentation table 310, values stored within the message story identifier 418 may point to data stored in a story table 314, and values stored within the message sender identifier 422 and the message receiver identifier 424 may point to user records stored within an entity table 306.

Figure 5:
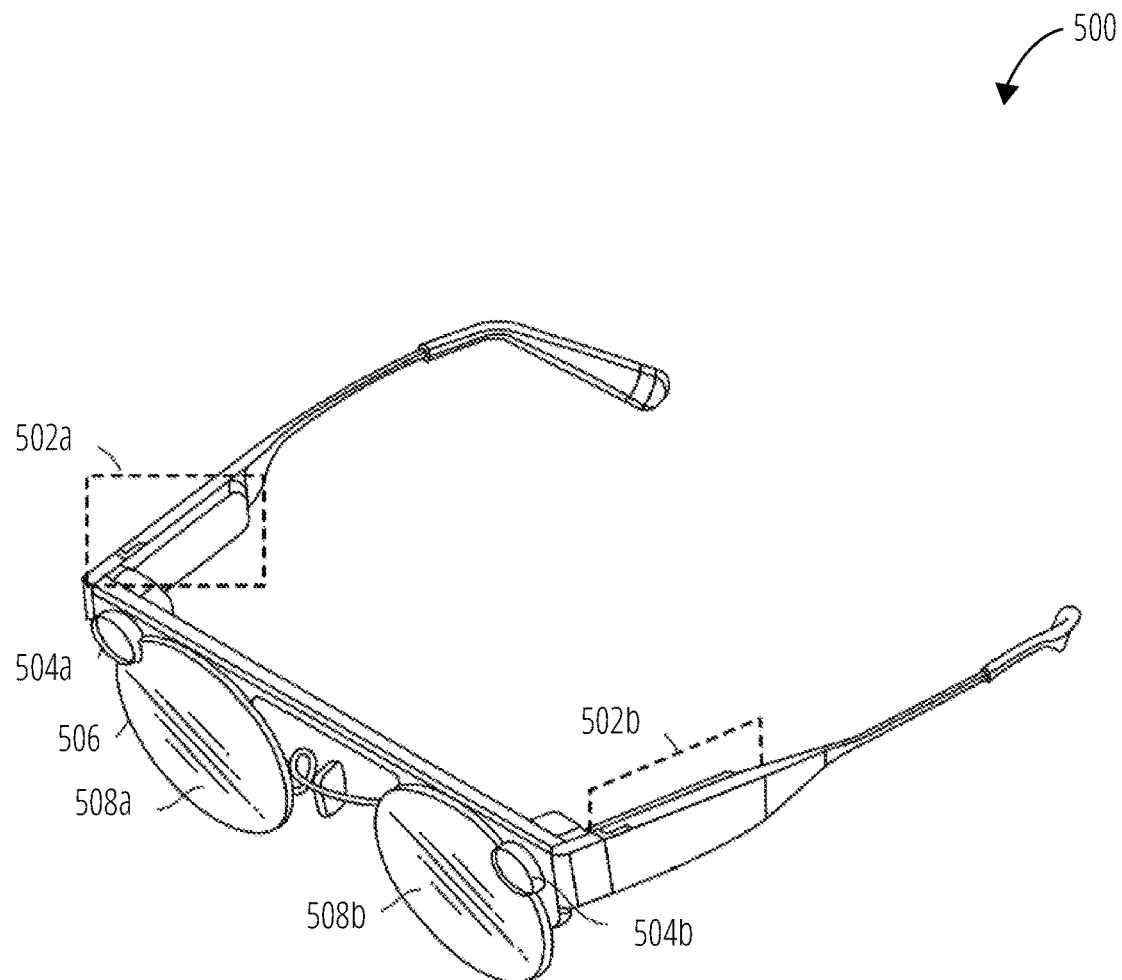
FIG. 5 illustrates a head-wearable apparatus comprising a media capture system, according to one example embodiment

FIG. 5 illustrates a head-wearable apparatus 500 comprising a media capture system 130, according to one example embodiment. FIG. 5 illustrates a perspective view of the head-wearable apparatus 500 according to one example embodiment. In FIG. 5, the head-wearable apparatus 500 is a pair of eyeglasses. In some embodiments, the head-wearable apparatus 500 can be sunglasses or goggles. Some embodiments can include one or more wearable devices, such as a pendant with an integrated camera that is integrated with, in communication with, or coupled to, the head-wearable apparatus 500 or a client device 102. Any desired wearable device may be used in conjunction with the embodiments of the present disclosure, such as a watch, a headset, a wristband, earbuds, clothing (such as a hat or jacket with integrated electronics), a clip-on electronic device, or any other wearable devices. It is understood that, while not shown, one or more portions of the system included in the head-wearable apparatus 500 can be included in a client device 102 (e.g., machine 700 in FIG. 7) that can be used in conjunction with the head-wearable apparatus 500.

In FIG. 5, the head-wearable apparatus 500 is a pair of eyeglasses that includes a frame 506 that includes eye wires (or rims) that are coupled to two stems (or temples), respectively, via hinges and/or end pieces. The eye wires of the frame 506 carry or hold a pair of lenses (e.g., lens 508a and lens 508b). The frame 506 includes a first (e.g., right) side that is coupled to the first stem and a second (e.g., left) side that is coupled to the second stem. The first side is opposite the second side of the frame 506.

The head-wearable apparatus 500 further includes a camera module (not shown) that includes camera lenses (e.g., camera lens 504a, camera lens 504b) and at least one image sensor. The camera lens 504a and camera lens 504b may be a perspective camera lens or a non-perspective camera lens. A non-perspective camera lens may be, for example, a fisheye lens, a wide-angle lens, an omnidirectional lens, etc. The image sensor captures digital video through the camera lens 504a and camera lens 504b. The images may be a still image frame or a video including a plurality of still image frames. The camera module can be coupled to the frame 506. As shown in FIG. 5, the frame 506 is coupled to the camera lens 504a and camera lens 504b such that the camera lenses (e.g., camera lens 504a, camera lens 504b) face forward. The camera lens 504a and camera lens 504b can be perpendicular to the lens 508a and lens 508b. The camera module can include dual-front facing cameras that are separated by the width of the frame 506 or the width of the head of the user of the head-wearable apparatus 500. The camera module can also include camera lenses that are rear-facing (not pictured).

In FIG. 5, the two stems (or temples) are respectively coupled to microphone housing 502a and microphone housing 502b. The first and second stems are coupled to opposite sides of a frame 506 of the head-wearable apparatus 500. The first stem is coupled to the first microphone housing 502a and the second stem is coupled to the second microphone housing 502b. The microphone housing 502a and microphone housing 502b can be coupled to the stems between the locations of the frame 506 and the temple tips. The microphone housing 502a and microphone housing 502b can be located on either side of the user's temples when the user is wearing the head-wearable apparatus 500.

As shown in FIG. 5, the microphone housing 502a and microphone housing 502b encase a plurality of microphones (not shown). The microphones are air interface sound pickup devices that convert sound into an electrical signal. More specifically, the microphones are transducers that convert acoustic pressure into electrical signals (e.g., acoustic signals). Microphones can be digital or analog microelectro-mechanical systems (MEMS) microphones. The acoustic signals generated by the microphones can be pulse density modulation (PDM) signals.

The head-wearable apparatus 500 may further include biometric sensors (not shown) that measure biometric sensor data. The biometric sensors may comprise sensors to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like.

Although the described flowchart below can show operations as a sequential process, many of the operations can be performed in parallel or concurrently. In addition, the order of the operations may be re-arranged. A process is terminated when its operations are completed. A process may correspond to a method, a procedure, an algorithm, etc. The operations of methods may be performed in whole or in part, may be performed in conjunction with some or all of the operations in other methods, and may be performed by any number of different systems, such as the systems described herein, or any portion thereof, such as a processor included in any of the systems.

Figure 6:
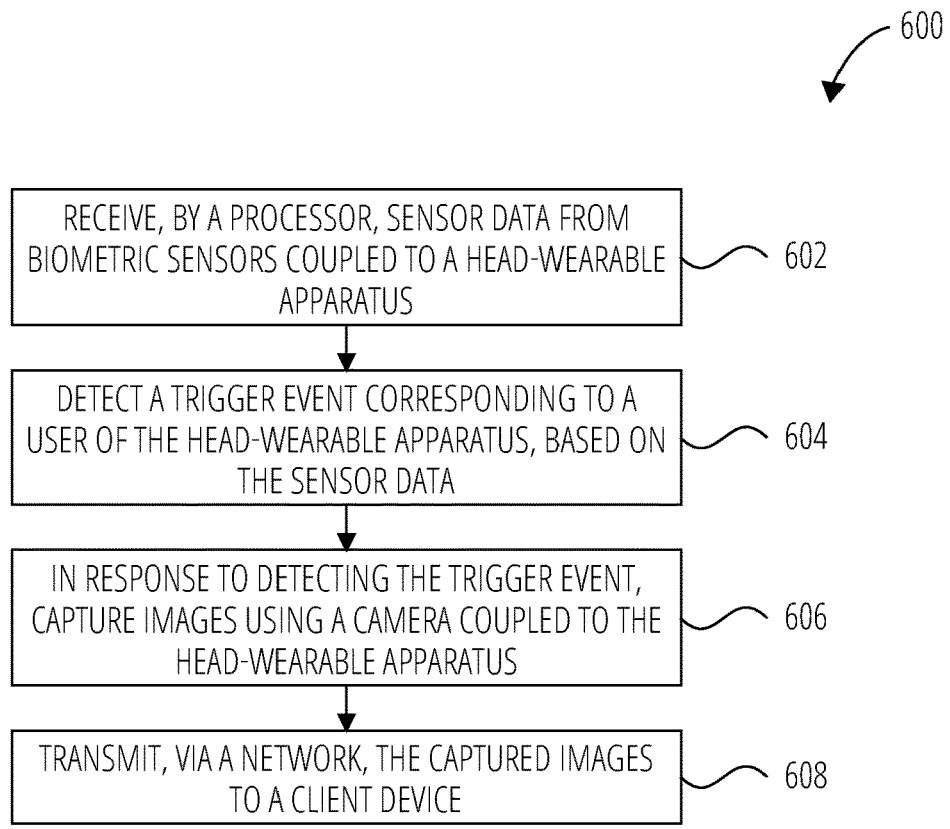
FIG. 6 is a flowchart of a method for automatically capturing images based on biometric sensor data of a wearable device, according to an example embodiment.

FIG. 6 is a flowchart of a method 600 for automatic media capture on a head-wearable apparatus 500 based on biometric sensor data, according to example embodiments. Some or all of the operations of the method 600 may be performed by the media capture system 130, a processor of the media capture system 130 or a combination thereof.

At operation 602, the media capture system 130 receives, by a processor, sensor data from biometric sensors coupled to a head-wearable apparatus. The biometric sensors are configured to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like.

At operation 604, the media capture system 130 detects a trigger event corresponding to a user of the head-wearable apparatus based on the sensor data. Detecting the trigger event may comprise detecting a change in the sensor data from the biometric sensors that exceeds a threshold. The change in the sensor data may be a change in the sensor data of one or more of the biometric sensors. The threshold amount may be predefined for each sensor of the biometric sensors. In some examples, the change in the sensor data must occur within a predefined amount of time (e.g., under 2 seconds) in order for the media capture system 130 to detect a trigger event. For example, the media capture system 130 may detect a sudden increase or drop in a heart rate of the user of the head-wearable apparatus 500.

At operation 606, in response to detecting the trigger event, the media capture system 130 captures images using a camera coupled to the head-wearable apparatus. In some examples the media capture system 130 captures audio and video in response to detecting the trigger event. The camera may be a front facing camera coupled to the head-wearable apparatus 500. In some examples, the media capture system 130 captures a second set of images facing the user of the head-wearable apparatus 500 using a second camera coupled to the head-wearable apparatus 500.

At operation 608, the media capture system 130 transmits, via a network, the captured images to a client device. For example, the captured images may be transmitted a contact of the user of the head-wearable apparatus 500. In some examples, the captured images are transmitted to a plurality of client devices. For example, the captured images may be transmitted to emergency contacts of the user of the head-wearable apparatus 500. The captured images may further be stored on a server system (e.g., messaging server system 108).

In some examples, the media capture system 130 transmits an alert to a plurality of client devices. The alert may comprise the captured images. In some examples, the alert comprises location data associated with the head-wearable apparatus 500.

Machine Architecture

Figure 7:
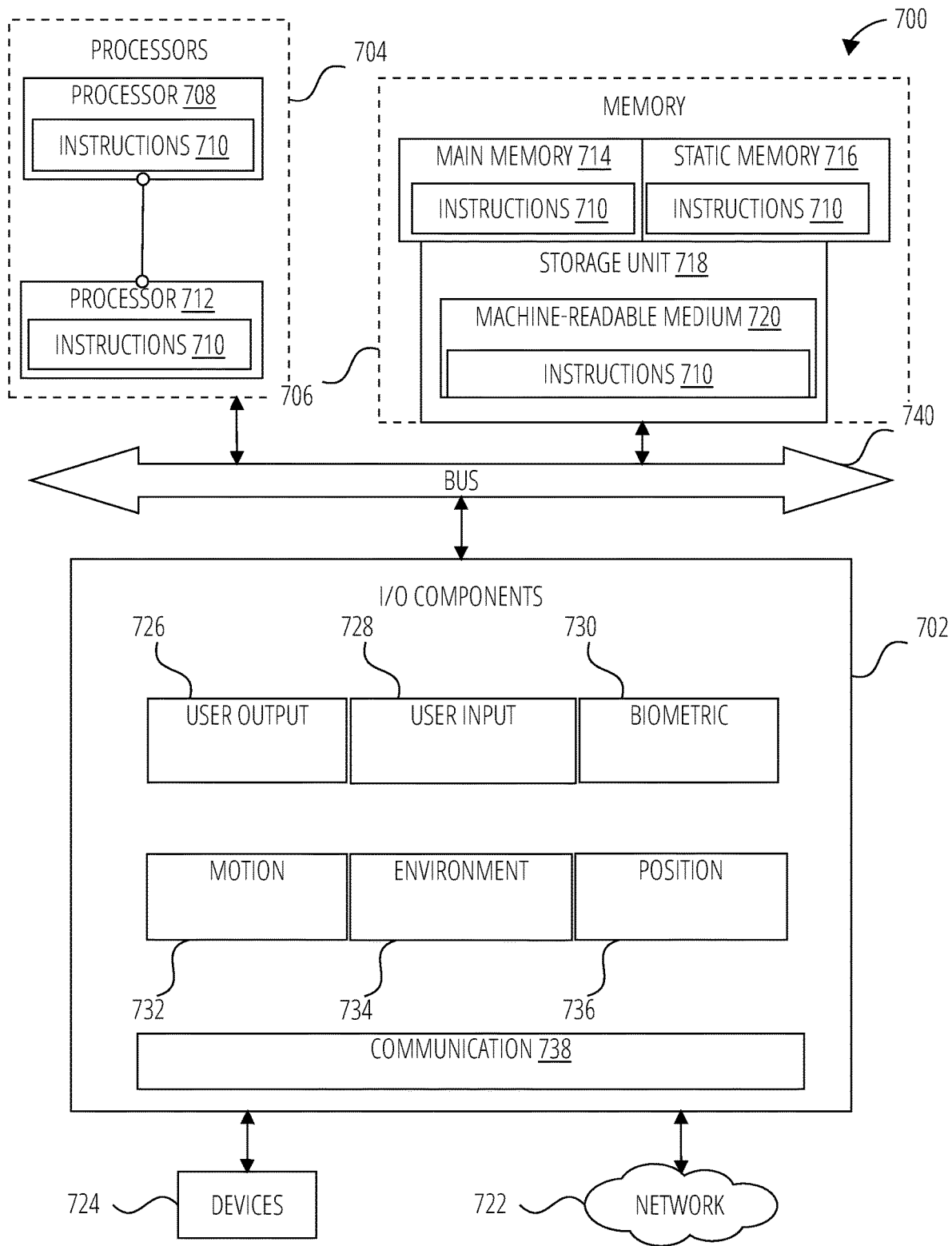
FIG. 7 is a diagrammatic representation of a machine in the form of a computer system within which a set of instructions may be executed for causing the machine to perform any one or more of the methodologies discussed herein, in accordance with some examples.

FIG. 7 is a diagrammatic representation of the machine 700 within which instructions 710 (e.g., software, a program, an application, an applet, an app, or other executable code) for causing the machine 700 to perform any one or more of the methodologies discussed herein may be executed. For example, the instructions 710 may cause the machine 700 to execute any one or more of the methods described herein. The instructions 710 transform the general, non-programmed machine 700 into a particular machine 700 programmed to carry out the described and illustrated functions in the manner described. The machine 700 may operate as a standalone device or may be coupled (e.g., networked) to other machines. In a networked deployment, the machine 700 may operate in the capacity of a server machine or a client machine in a server-client network environment, or as a peer machine in a peer-to-peer (or distributed) network environment. The machine 700 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 710, sequentially or otherwise, that specify actions to be taken by the machine 700. Further, while only a single machine 700 is illustrated, the term "machine" shall also be taken to include a collection of machines that individually or jointly execute the instructions 710 to perform any one or more of the methodologies discussed herein. The machine 700, for example, may comprise the client device 102 or any one of a number of server devices forming part of the messaging server system 108. In some examples, the machine 700 may also comprise both client and server systems, with certain operations of a particular method or algorithm being performed on the server-side and with certain operations of the particular method or algorithm being performed on the client-side.

The machine 700 may include processors 704, memory 706, and input/output I/O components 702, which may be configured to communicate with each other via a bus 740. In an example, the processors 704 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 708 and a processor 712 that execute the instructions 710. The term "processor" is intended to include multi-core processors that may comprise two or more independent processors (sometimes referred to as "cores") that may execute instructions contemporaneously. Although FIG. 7 shows multiple processors 704, the machine 700 may include a single processor with a single-core, a single processor with multiple cores (e.g., a multi-core processor), multiple processors with a single core, multiple processors with multiples cores, or any combination thereof.

The memory 706 includes a main memory 714, a static memory 716, and a storage unit 718, both accessible to the processors 704 via the bus 740. The main memory 706, the static memory 716, and storage unit 718 store the instructions 710 embodying any one or more of the methodologies or functions described herein. The instructions 710 may also reside, completely or partially, within the main memory 714, within the static memory 716, within machine-readable medium 720 within the storage unit 718, within at least one of the processors 704 (e.g., within the Processor's cache memory), or any suitable combination thereof, during execution thereof by the machine 700.

The I/O components 702 may include a wide variety of components to receive input, provide output, produce output, transmit information, exchange information, capture measurements, and so on. The specific I/O components 702 that are included in a particular machine will depend on the type of machine. For example, portable machines such as mobile phones may include a touch input device or other such input mechanisms, while a headless server machine will likely not include such a touch input device. It will be appreciated that the I/O components 702 may include many other components that are not shown in FIG. 7. In various examples, the I/O components 702 may include user output components 726 and user input components 728. The user output components 726 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 728 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 702 may include biometric components 730, motion components 732, environmental components 734, or position components 736, among a wide array of other components. For example, the biometric components 730 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 732 include acceleration sensor components (e.g., accelerometer), gravitation sensor components, rotation sensor components (e.g., gyroscope).

The environmental components 734 include, for example, one or cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

With respect to cameras, the client device 102 may have a camera system comprising, for example, front cameras on a front surface of the client device 102 and rear cameras on a rear surface of the client device 102. The front cameras may, for example, be used to capture still images and video of a user of the client device 102 (e.g., "selfies"), which may then be augmented with augmentation data (e.g., filters) described above. The rear cameras may, for example, be used to capture still images and videos in a more traditional camera mode, with these images similarly being augmented with augmentation data. In addition to front and rear cameras, the client device 102 may also include a 360° camera for capturing 360° photographs and videos.

Further, the camera system of a client device 102 may include dual rear cameras (e.g., a primary camera as well as a depth-sensing camera), or even triple, quad or penta rear camera configurations on the front and rear sides of the client device 102. These multiple cameras systems may include a wide camera, an ultra-wide camera, a telephoto camera, a macro camera and a depth sensor, for example.

The position components 736 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 702 further include communication components 738 operable to couple the machine 700 to a network 722 or devices 724 via respective coupling or connections. For example, the communication components 738 may include a network interface Component or another suitable device to interface with the network 722. In further examples, the communication components 738 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 724 may be another machine or any of a wide variety of peripheral devices (e.g., a peripheral device coupled via a USB).

Moreover, the communication components 738 may detect identifiers or include components operable to detect identifiers. For example, the communication components 738 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 738, such as location via Internet Protocol (IP) geolocation, location via Wi-Fi® signal triangulation, location via detecting an NFC beacon signal that may indicate a particular location, and so forth.

The various memories (e.g., main memory 714, static memory 716, and memory of the processors 704) and storage unit 718 may store one or more sets of instructions and data structures (e.g., software) embodying or used by any one or more of the methodologies or functions described herein. These instructions (e.g., the instructions 710), when executed by processors 704, cause various operations to implement the disclosed examples.

The instructions 710 may be transmitted or received over the network 722, using a transmission medium, via a network interface device (e.g., a network interface component included in the communication components 738) and using any one of several well-known transfer protocols (e.g., hypertext transfer protocol (HTTP)). Similarly, the instructions 710 may be transmitted or received using a transmission medium via a coupling (e.g., a peer-to-peer coupling) to the devices 724.

Software Architecture

Figure 8:
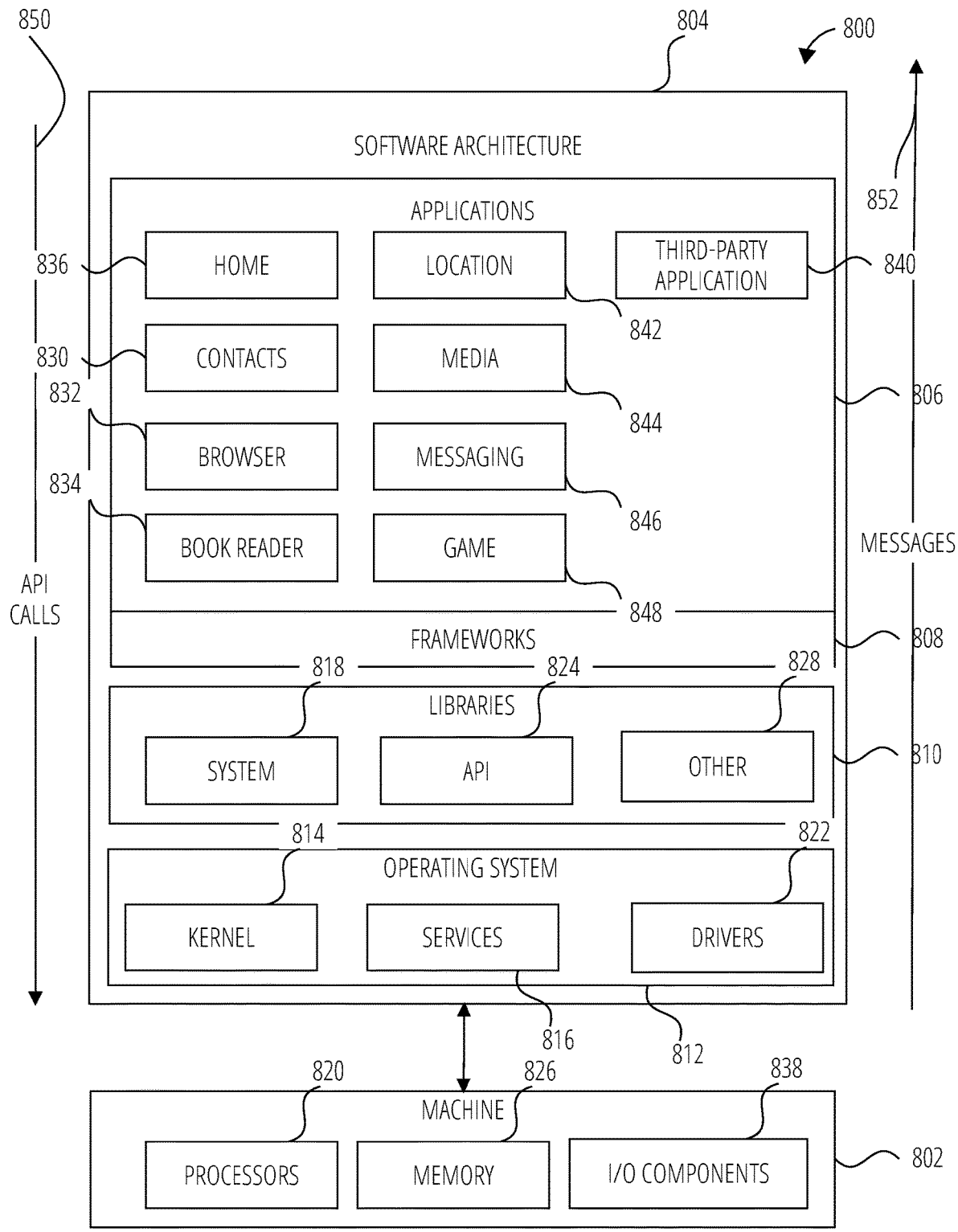
FIG. 8 is a block diagram showing a software architecture within which examples may be implemented.

FIG. 8 is a block diagram 800 illustrating a software architecture 804, which can be installed on any one or more of the devices described herein. The software architecture 804 is supported by hardware such as a machine 802 that includes processors 820, memory 826, and I/O components 838. In this example, the software architecture 804 can be conceptualized as a stack of layers, where each layer provides a particular functionality. The software architecture 804 includes layers such as an operating system 812, libraries 810, frameworks 808, and applications 806. Operationally, the applications 806 invoke API calls 850 through the software stack and receive messages 852 in response to the API calls 850.

The operating system 812 manages hardware resources and provides common services. The operating system 812 includes, for example, a kernel 814, services 816, and drivers 822. The kernel 814 acts as an abstraction layer between the hardware and the other software layers. For example, the kernel 814 provides memory management, processor management (e.g., scheduling), component management, networking, and security settings, among other functionality. The services 816 can provide other common services for the other software layers. The drivers 822 are responsible for controlling or interfacing with the underlying hardware. For instance, the drivers 822 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 810 provide a common low-level infrastructure used by the applications 806. The libraries 810 can include system libraries 818 (e.g., C standard library) that provide functions such as memory allocation functions, string manipulation functions, mathematic functions, and the like. In addition, the libraries 810 can include API libraries 824 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 810 can also include a wide variety of other libraries 828 to provide many other APIs to the applications 806.

The frameworks 808 provide a common high-level infrastructure that is used by the applications 806. For example, the frameworks 808 provide various graphical user interface (GUI) functions, high-level resource management, and high-level location services. The frameworks 808 can provide a broad spectrum of other APIs that can be used by the applications 806, some of which may be specific to a particular operating system or platform.

In an example, the applications 806 may include a home application 836, a contacts application 830, a browser application 832, a book reader application 834, a location application 842, a media application 844, a messaging application 846, a game application 848, and a broad assortment of other applications such as a third-party application 840. The applications 806 are programs that execute functions defined in the programs. Various programming languages can be employed to create one or more of the applications 806, structured in a variety of manners, such as object-oriented programming languages (e.g., Objective-C, Java, or C++) or procedural programming languages (e.g., C or assembly language). In a specific example, the third-party application 840 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 840 can invoke the API calls 850 provided by the operating system 812 to facilitate functionality described herein.

System With Head-Wearable Apparatus

Figure 9:
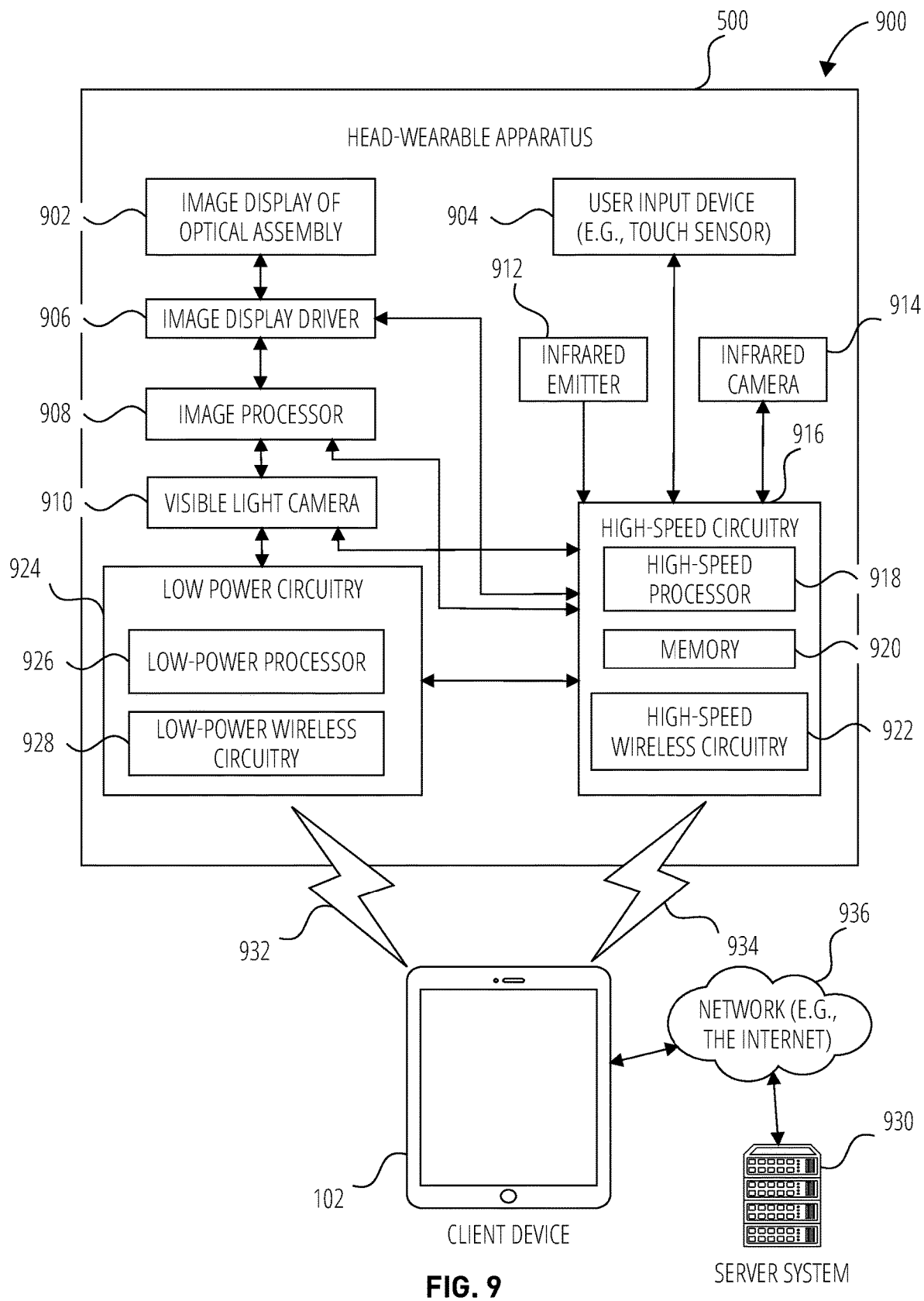
FIG. 9 illustrates a system in which the head-wearable apparatus can be implemented according to one example embodiment.

FIG. 9 illustrates a system 900 in which the head-wearable apparatus 500 can be implemented according to one example embodiment. FIG. 9 is a high-level functional block diagram of an example head-wearable apparatus 500 communicatively coupled a mobile client device 102 and a server system 930 via various network 936.

Head-wearable apparatus 500 includes a camera, such as at least one of visible light camera 910, infrared emitter 912 and infrared camera 914. The camera can include the camera module with the camera lens 504a and camera lens 504b in FIG. 5.

Client device 102 can be capable of connecting with head-wearable apparatus 500 using both a low-power wireless connection 932 and a high-speed wireless connection 934. Client device 102 is connected to server system 930 and network 936. The network 936 may include any combination of wired and wireless connections.

Head-wearable apparatus 500 further includes two image displays of the image display of optical assembly 902. The two image displays of optical assembly 902 include one associated with the left lateral side and one associated with the right lateral side of the head-wearable apparatus 500. Head-wearable apparatus 500 also includes image display driver 906, image processor 908, low-power low power circuitry 924, and high-speed circuitry 916. Image display of optical assembly 902 are for presenting images and videos, including an image that can include a graphical user interface to a user of the head-wearable apparatus 500.

Image display driver 906 commands and controls the image display of the image display of optical assembly 902. Image display driver 906 may deliver image data directly to the image display of the image display of optical assembly 902 for presentation or may have to convert the image data into a signal or data format suitable for delivery to the image display device. For example, the image data may be video data formatted according to compression formats, such as H.264 (MPEG-4 Part 10), HEVC, Theora, Dirac, RealVideo RV40, VP8, VP9, or the like, and still image data may be formatted according to compression formats such as Portable Network Group (PNG), Joint Photographic Experts Group (JPEG), Tagged Image File Format (TIFF) or exchangeable image file format (Exif) or the like.

As noted above, head-wearable apparatus 500 includes a frame 506 and stems (or temples) extending from a lateral side of the frame 506. Head-wearable apparatus 500 further includes a user input device 904 (e.g., touch sensor or push button) including an input surface on the head-wearable apparatus 500. The user input device 904 (e.g., touch sensor or push button) is to receive from the user an input selection to manipulate the graphical user interface of the presented image.

The components shown in FIG. 9 for the head-wearable apparatus 500 are located on one or more circuit boards, for example a PCB or flexible PCB, in the rims or temples. Alternatively or additionally, the depicted components can be located in the chunks, frames, hinges, or bridge of the head-wearable apparatus 500. Left and right visible light cameras 910 can include digital camera elements such as a complementary metal-oxide-semiconductor (CMOS) image sensor, charge coupled device, a camera lens 504a and camera lens 504b, or any other respective visible or light capturing elements that may be used to capture data, including images of scenes with unknown objects.

Head-wearable apparatus 500 includes a memory 920 which stores instructions to perform a subset or all of the functions described herein. Memory 920 can also include storage device.

As shown in FIG. 9, high-speed circuitry 916 includes high-speed processor 918, memory 920, and high-speed wireless circuitry 922. In the example, the image display driver 906 is coupled to the high-speed circuitry 916 and operated by the high-speed processor 918 in order to drive the left and right image displays of the image display of optical assembly 902. High-speed processor 918 may be any processor capable of managing high-speed communications and operation of any general computing system needed for head-wearable apparatus 500. High-speed processor 918 includes processing resources needed for managing high-speed data transfers on high-speed wireless connection 934 to a wireless local area network (WLAN) using high-speed wireless circuitry 922. In certain examples, the high-speed processor 918 executes an operating system such as a LINUX operating system or other such operating system of the head-wearable apparatus 500 and the operating system is stored in memory 920 for execution. In addition to any other responsibilities, the high-speed processor 918 executing a software architecture for the head-wearable apparatus 500 is used to manage data transfers with high-speed wireless circuitry 922. In certain examples, high-speed wireless circuitry 922 is configured to implement Institute of Electrical and Electronic Engineers (IEEE) 802.11 communication standards, also referred to herein as Wi-Fi. In other examples, other high-speed communications standards may be implemented by high-speed wireless circuitry 922.

Low-power wireless circuitry 928 and the high-speed wireless circuitry 922 of the head-wearable apparatus 500 can include short range transceivers (Bluetooth™) and wireless wide, local, or wide area network transceivers (e.g., cellular or WiFi). Client device 102, including the transceivers communicating via the low-power wireless connection 932 and high-speed wireless connection 934, may be implemented using details of the architecture of the head-wearable apparatus 500, as can other elements of network 936.

Memory 920 includes any storage device capable of storing various data and applications, including, among other things, camera data generated by the left and right visible light cameras 910, infrared camera 914, and the image processor 908, as well as images generated for display by the image display driver 906 on the image displays of the image display of optical assembly 902. While memory 920 is shown as integrated with high-speed circuitry 916, in other examples, memory 920 may be an independent stand-alone element of the head-wearable apparatus 500. In certain such examples, electrical routing lines may provide a connection through a chip that includes the high-speed processor 918 from the image processor 908 or low-power processor 926 to the memory 920. In other examples, the high-speed processor 918 may manage addressing of memory 920 such that the low-power processor 926 will boot the high-speed processor 918 any time that a read or write operation involving memory 920 is needed.

As shown in FIG. 9, the low-power processor 926 or high-speed processor 918 of the head-wearable apparatus 500 can be coupled to the camera (visible light camera 910; infrared emitter 912, or infrared camera 914), the image display driver 906, the user input device 904 (e.g., touch sensor or push button), and the memory 920.

Head-wearable apparatus 500 is connected with a host computer. For example, the head-wearable apparatus 500 is paired with the client device 102 via the high-speed wireless connection 934 or connected to the server system 930 via the network 936. Server system 930 may be one or more computing devices as part of a service or network computing system, for example, that include a processor, a memory, and network communication interface to communicate over the network 936 with the client device 102 and head-wearable apparatus 500.

The client device 102 includes a processor and a network communication interface coupled to the processor. The network communication interface allows for communication over the network 936, low-power wireless connection 932 or high-speed wireless connection 934. Client device 102 can further store at least portions of the instructions for generating a binaural audio content in the client device 102's memory to implement the functionality described herein.

Output components of the head-wearable apparatus 500 include visual components, such as a display such as a liquid crystal display (LCD), a plasma display panel (PDP), a light emitting diode (LED) display, a projector, or a waveguide. The image displays of the optical assembly are driven by the image display driver 906. The output components of the head-wearable apparatus 500 further include acoustic components (e.g., speakers), haptic components (e.g., a vibratory motor), other signal generators, and so forth. The input components of the head-wearable apparatus 500, the client device 102, and server system 930, such as the user input device 904, may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instruments), tactile input components (e.g., a physical button, a touch screen that provides location and force of touches or touch gestures, or other tactile input components), audio input components (e.g., a microphone), and the like.

Head-wearable apparatus 500 may optionally include additional peripheral device elements. Such peripheral device elements may include biometric sensors, additional sensors, or display elements integrated with head-wearable apparatus 500. For example, peripheral device elements may include any I/O components including output components, motion components, position components, or any other such elements described herein.

For example, the biometric components include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components include acceleration sensor components (e.g., accelerometer), gravitation sensor components, rotation sensor components (e.g., gyroscope), and so forth. The position components include location sensor components to generate location coordinates (e.g., a Global Positioning System (GPS) receiver component), WiFi or Bluetooth™ transceivers to generate positioning system coordinates, altitude sensor components (e.g., altimeters or barometers that detect air pressure from which altitude may be derived), orientation sensor components (e.g., magnetometers), and the like. Such positioning system coordinates can also be received over low-power wireless connections 932 and high-speed wireless connection 934 from the client device 102 via the low-power wireless circuitry 928 or high-speed wireless circuitry 922.

Where a phrase similar to "at least one of A, B, or C," "at least one of A, B, and C," "one or more A, B, or C," or "one or more of A, B, and C" is used, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Changes and modifications may be made to the disclosed embodiments without departing from the scope of the present disclosure. These and other changes or modifications are intended to be included within the scope of the present disclosure, as expressed in the following claims.

GLOSSARY

"Carrier signal" refers to any intangible medium that is capable of storing, encoding, or carrying instructions for execution by the machine, and includes digital or analog communications signals or other intangible media to facilitate communication of such instructions. Instructions may be transmitted or received over a network using a transmission medium via a network interface device.

"Client device" refers to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

"Communication network" refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

"Component" refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering examples in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In examples in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some examples, the processors or processor-implemented components may be located in a single geographic location (e.g., within a home environment, an office environment, or a server farm). In other examples, the processors or processor-implemented components may be distributed across a number of geographic locations.

"Computer-readable storage medium" refers to both machine-storage media and transmission media. Thus, the terms include both storage devices/media and carrier waves/modulated data signals. The terms "machine-readable medium," "computer-readable medium" and "device-readable medium" mean the same thing and may be used interchangeably in this disclosure.

"Ephemeral message" refers to a message that is accessible for a time-limited duration. An ephemeral message may be a text, an image, a video and the like. The access time for the ephemeral message may be set by the message sender. Alternatively, the access time may be a default setting or a setting specified by the recipient. Regardless of the setting technique, the message is transitory.

"Machine storage medium" refers to a single or multiple storage devices and media (e.g., a centralized or distributed database, and associated caches and servers) that store executable instructions, routines and data. The term shall accordingly be taken to include, but not be limited to, solid-state memories, and optical and magnetic media, including memory internal or external to processors. Specific examples of machine-storage media, computer-storage media and device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms "machine-storage medium," "device-storage medium," "computer-storage medium" mean the same thing and may be used interchangeably in this disclosure. The terms "machine-storage media," "computer-storage media," and "device-storage media" specifically exclude carrier waves, modulated data signals, and other such media, at least some of which are covered under the term "signal medium."

"Non-transitory computer-readable storage medium" refers to a tangible medium that is capable of storing, encoding, or carrying the instructions for execution by a machine.

"Signal medium" refers to any intangible medium that is capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

What is claimed is:

1. A method comprising:
    communicating, by at least one processor, with a plurality of computing devices in a chat session via a head-wearable apparatus;
    receiving sensor data from biometric sensors coupled to the head-wearable apparatus during the chat session;
    detecting a trigger event corresponding to a user of the head-wearable apparatus based on a decrease in a biosignal of the sensor data transgressing a predefined threshold within a predefined amount of time;
    in response to detecting the trigger event, capturing images using a camera coupled to the head-wearable apparatus; and
    transmitting, via the chat session, the captured images to the plurality of computing devices.

2. The method of claim 1, wherein detecting the trigger event comprises:
    detecting a first heart rate of the user at a first time; and
    detecting a second heart rate of the user at a second time, the decrease being between the first heart rate and the second heart rate, and a difference between the first time and the second time being between the predefined amount of time.

3. The method of claim 1, wherein the biometric sensors comprise a first set of sensors configured to detect facial and body gestures, a second set of sensors configured to measure biosignals and a third set of sensors configured to identify a person.

4. The method of claim 1, wherein the camera is a front-facing camera.

5. The method of claim 1, wherein the capturing images further comprises:
    capturing a second set of images from a second camera facing the user of the head-wearable apparatus.

6. The method of claim 1, the method further comprising:
    in response to detecting the trigger event, causing a microphone coupled to the head-wearable apparatus to record audio.

7. The method of claim 1, the method further comprising:
    transmitting an alert to the plurality of computing devices, the alert comprising the captured images and location data associated with the head-wearable apparatus.

8. The method of claim 1, wherein detecting the trigger event comprises:
    detecting expressions of the user based on the sensor data from the biometric sensors; and
    detecting a change in the expressions based on the sensor data.

9. A system comprising:
    at least one processor; and
    a memory storing instructions that, when executed by the at least one processor, cause the system to perform operations comprising:
        communicating with a plurality of computing devices in a chat session via a head-wearable apparatus;
        receiving sensor data from biometric sensors coupled to the head-wearable apparatus during the chat session;
        detecting a trigger event corresponding to a user of the head-wearable apparatus based on a decrease in a biosignal of the sensor data transgressing a predefined threshold within a predefined amount of time;

in response to detecting the trigger event, capturing images using a camera coupled to the head-wearable apparatus; and transmitting, via the chat session, the captured images to the plurality of computing devices.

10. The system of claim 9, wherein detecting the trigger event comprises:

detecting a first heart rate of the user at a first time; and detecting a second heart rate of the user at a second time, the decrease being between the first heart rate and the second heart rate, and a difference between the first time and the second time being between the predefined amount of time.

11. The system of claim 9, wherein the biometric sensors comprises a first set of sensors configured to detect facial and body gestures, a second set of sensors configured to measure biosignals and a third set of sensors configured to identify a person.

12. The system of claim 9, wherein the camera is a front-facing camera.

13. The system of claim 9, wherein the capturing images further comprises:

capturing a second set of images from a second camera facing the user of the head-wearable apparatus.

14. The system of claim 9, wherein the operations further comprise:

in response to detecting the trigger event, causing a microphone coupled to the head-wearable apparatus to record audio.

15. The system of claim 9, wherein the operations further comprise:

transmitting an alert to the plurality of computing devices, the alert comprising the captured images and location data associated with the head-wearable apparatus.

16. The system of claim 9, wherein detecting the trigger event comprises:

detecting expressions of the user based on the sensor data from the biometric sensors; and detecting a change in the expressions based on the sensor data.

17. A non-transitory computer-readable storage medium, the computer-readable storage medium including instructions that when executed by a computer, cause the computer to perform operations comprising:

communicating with a plurality of computing devices in a chat session via a head-wearable apparatus;

receiving sensor data from biometric sensors coupled to a head-wearable apparatus during the chat session;

detecting a trigger event corresponding to a user of the head-wearable apparatus based on a decrease in a biosignal of the sensor data transgressing a predefined threshold within a predefined amount of time;

in response to detecting the trigger event, capturing images using a camera coupled to the head-wearable apparatus; and transmitting, via the chat session, the captured images to the plurality of computing devices.

18. The non-transitory computer-readable storage medium of claim 17, wherein detecting the trigger event comprises:

detecting a first heart rate of the user at a first time; and detecting a second heart rate of the user at a second time, the decrease being between the first heart rate and the second heart rate, and a difference between the first time and the second time being between the predefined amount of time.

19. The non-transitory computer-readable storage medium of claim 17, wherein the biometric sensors comprises a first set of sensors configured to detect facial and body gestures, a second set of sensors configured to measure biosignals and a third set of sensors configured to identify a person.

20. The non-transitory computer-readable storage medium of claim 17, wherein the camera is a front-facing camera.

* * * * *